US010315038B2

(12) United States Patent
Suryavanshi

(10) Patent No.: US 10,315,038 B2
(45) Date of Patent: Jun. 11, 2019

(54) CLINICAL GUIDANCE USER INTERFACES FOR NEUROSTIMULATOR PROGRAMMING

(71) Applicant: Boston Scientific Neuromodulation Corporation, Valencia, CA (US)

(72) Inventor: Annasaheb Suryavanshi, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 15/433,886

(22) Filed: Feb. 15, 2017

(65) Prior Publication Data

US 2017/0239486 A1 Aug. 24, 2017

Related U.S. Application Data

(60) Provisional application No. 62/297,219, filed on Feb. 19, 2016.

(51) Int. Cl.
*A61N 1/372* (2006.01)
*A61N 1/36* (2006.01)
*G16H 40/40* (2018.01)
*G06F 19/00* (2018.01)

(52) U.S. Cl.
CPC ..... *A61N 1/37247* (2013.01); *A61N 1/36071* (2013.01); *A61N 1/36146* (2013.01); *A61N 1/37264* (2013.01); *G06F 19/00* (2013.01); *G16H 40/40* (2018.01)

(58) Field of Classification Search
None
See application file for complete search history.

(56) References Cited

U.S. PATENT DOCUMENTS

| | | | |
|---|---|---|---|
| 5,716,382 A * | 2/1998 | Snell | G06F 19/00 607/30 |
| 7,035,690 B2 | 4/2006 | Goetz | |
| 7,096,067 B2 | 8/2006 | Linberg | |
| 7,181,286 B2 * | 2/2007 | Sieracki | A61N 1/08 607/48 |
| 7,676,273 B2 | 3/2010 | Goetz et al. | |

(Continued)

*Primary Examiner* — Kennedy Schaetzle
(74) *Attorney, Agent, or Firm* — Schwegman Lundberg & Woessner, P.A.

(57) ABSTRACT

An example of a system may include a processor and a memory device comprising instructions, which when executed by the processor, cause the processor to receive, in a graphical user interface, a clinician input of physiological information and therapy information for neurostimulation treatment of a human subject using a neurostimulation device, and request a neurostimulation program corresponding to the physiological information and the therapy information from a remote programming guidance information system. For example, program data of a neurostimulation program may be provided from the programming guidance information system, selected on the basis of a best match to the physiological information and the therapy information. A representation of the program data and the parameters of the neurostimulation program may be displayed in the graphical user interface, including ratings, comments, and other characteristics of the neurostimulation program that are maintained by the remote programming guidance information system.

19 Claims, 10 Drawing Sheets

(56) References Cited

U.S. PATENT DOCUMENTS

| | | |
|---|---|---|
| 7,848,819 B2 | 12/2010 | Goetz |
| 7,933,656 B2 | 4/2011 | Sieracki et al. |
| 2008/0103533 A1* | 5/2008 | Patel .................. A61N 1/36082 607/2 |
| 2012/0215295 A1 | 8/2012 | Pianca |
| 2013/0023950 A1 | 1/2013 | Gauthier |
| 2014/0107567 A1* | 4/2014 | Goetz .................. A61B 5/0031 604/66 |
| 2014/0277261 A1* | 9/2014 | Rao .................... A61N 1/37247 607/46 |
| 2014/0277284 A1 | 9/2014 | Chen et al. |
| 2014/0365654 A1 | 12/2014 | Huerto et al. |
| 2015/0217116 A1 | 8/2015 | Parramon et al. |

* cited by examiner

800

810 Physiological Information

| Nature of Pain | Injury, Sharp |
| Pain Location | Lumbar, L3-L4 |
| Pain Intensity | Moderate (6 of 10) |
| Pain Spread | Minimal |

820 Therapy Information

| Number of Leads | 8 |
| Device | Device Model XYZ |

Electrode Placement Location

830 Available Programs

Program A — 840a

Relevancy Rating: 97%

Indications:

Device Placement:

Rating: 4.3 of 5

Comments: — 850a

[ Load Program ]

Program B — 840b

Relevancy Rating: 97%

Indications:

Device Placement:

Rating: 4.3 of 5

Comments: — 850b

[ Load Program ]

*FIG. 8*

CLINICAL GUIDANCE USER INTERFACES FOR NEUROSTIMULATOR PROGRAMMING

PRIORITY CLAIM

This application claims the priority benefit of U.S. Provisional Application Ser. No. 62/297,219, filed Feb. 19, 2016, which is hereby incorporated by reference in its entirety.

TECHNICAL FIELD

The present disclosure relates generally to medical devices, and more particularly, to systems, devices, and methods for electrical stimulation programming techniques.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

The neurostimulation energy may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

Example 1 includes subject matter (such as a device, apparatus, or machine) comprising: a processor; and a memory device comprising instructions, which when executed by the processor, cause the processor to: receive, in a graphical user interface, a clinician input of physiological information and therapy information for neurostimulation treatment of a human subject using a neurostimulation device; request, from a programming guidance information system, a neurostimulation program corresponding to the physiological information and the therapy information; receive, from the programming guidance information system, program data of the neurostimulation program corresponding to the physiological information and the therapy information; and output, in the graphical user interface, a representation of the program data of the neurostimulation program corresponding to the physiological information and the therapy information; wherein the neurostimulation program includes a plurality of programmable parameter settings for operational control of the neurostimulation device, and wherein the program data includes respective parameter values established for the plurality of programmable parameter settings.

In Example 2, the subject matter of Example 1 may include, the request for the neurostimulation program being communicated to the programming guidance information system, the request including data that represents the physiological information and data that represents the therapy information, wherein the physiological information indicates one or more of: a medical condition, pain, or medical symptoms of the human subject, and wherein the therapy information indicates one or more of: a type of the neurostimulation device, a state of the neurostimulation device, respective locations for placements of leads of the neurostimulation device in the human subject, or a type of the leads and a number of the leads of the neurostimulation device in the human subject.

In Example 3, the subject matter of any one or more of Examples 1-2 may include, the plurality of programmable parameter settings including settings for one or more of: pulse patterns, pulse shapes, or a spatial location, of pulses of modulated energy provided with a plurality of leads of the neurostimulation device.

In Example 4, the subject matter of Example 3 may include, the plurality of programmable parameter settings including settings for two or more of: a frequency, a pulse width, a number of pulses within a burst or train of pulses, the train-to-train interval, the burst frequency of trains of pulses, a pulse duty cycle, or a burst duty cycle, of the pulses of modulated energy provided with the plurality of leads of the neurostimulation device.

In Example 5, the subject matter of any one or more of Examples 1-4 may include, the processor further to: receive, from the programming guidance information system, rating data and comment data for the neurostimulation program corresponding to the physiological information and the therapy information; wherein the representation of the program data includes a representation of the rating data and the comment data in the graphical user interface, the representation to depict respective clinician ratings and comments provided for respective implementations of the neurostimulation program.

In Example 6, the subject matter of Example 5 may include, the representation of the program data including a listing of the neurostimulation program and a plurality of additional neurostimulation programs, the additional neurostimulation programs corresponding to the physiological information and the therapy information, and wherein the listing is ordered based on the respective clinician ratings and comments for the respective neurostimulation programs.

In Example 7, the subject matter of any one or more of Examples 1-6 may include, the programming guidance information system being accessible to the system via a network connection, and wherein the programming guidance information system includes a data interface accessible via the network connection to receive the request for the neurostimulation program and transmit the program data of the neurostimulation program to the system in response to the request, and wherein the programming guidance information system is operable to select the neurostimulation program from among a plurality of candidate neurostimulation programs represented in remote data storage accessible to the programming guidance information system.

In Example 8, the subject matter of Example 7 may include, the neurostimulation program being selected by the programming guidance information system based on a number of matches of a plurality of characteristics of the physiological information and the therapy information to characteristics of the neurostimulation program, and wherein the number of matches for the neurostimulation program exceeds a number of matches of the plurality of candidate neurostimulation programs with the plurality of characteristics for the physiological information and the therapy information.

In Example 9, the subject matter of any one or more of Examples 1-8 may include, the program data being provided from the system for use in an initial programming of the neurostimulation device, and wherein an update to the neurostimulation program is provided from clinician modification of one or more of the plurality of programmable parameter settings.

In Example 10, the subject matter of Example 9 may include, the processor further to: receive, in the graphical user interface, a clinician input of a rating and a comment for the update to the neurostimulation program; transmit, to the programming guidance information system, updated program data for the update to the neurostimulation program; and transmit, to the programming guidance information system, data representing the rating and the comment for the update to the neurostimulation program.

In Example 11, the subject matter of any one or more of Examples 1-10 may include, the graphical user interface being a browser web application adapted for output with a browser of a computing device that includes the processor and memory, and wherein the graphical user interface provides an input screen to receive the clinician input of the physiological information and the therapy information and an output screen to output the representation of the program data of the neurostimulation program.

In Example 12, the subject matter of any one or more of Examples 1-11 may include, the graphical user interface being a software app adapted for native execution by an operating system of a computing device that includes the processor and memory, and wherein the graphical user interface provides an input screen to receive the clinician input of the physiological information and the therapy information and an output screen to output the representation of the program data of the neurostimulation program.

In Example 13, the subject matter of any one or more of Examples 1-12 may include, the processor further to: transmit the plurality of programmable parameter settings to a programming device, the programming device to program the neurostimulator device using the plurality of programmable parameter settings.

Example 14 is a machine-readable medium including instructions, which when executed by a machine, cause the machine to perform operations of any of the Examples 1 to 13.

Example 15 is a method to perform electronic operations of any of the Examples 1 to 13.

Example 16 includes subject matter (such as a device, apparatus, or machine), comprising: user interface processing circuitry, implemented with a processor and a memory, the user interface processing circuitry to perform electronic operations to: receive, in a graphical user interface, a clinician input of physiological information and therapy information for neurostimulation treatment of a human subject using a neurostimulation device; request, from a programming guidance information system, a neurostimulation program corresponding to the physiological information and the therapy information; receive, from the programming guidance information system, program data of the neurostimulation program corresponding to the physiological information and the therapy information; and output, in the graphical user interface, a representation of the program data of the neurostimulation program corresponding to the physiological information and the therapy information; wherein the neurostimulation program includes a plurality of programmable parameter settings for operational control of the neurostimulation device, and wherein the program data includes respective parameter values established for the plurality of programmable parameter settings.

In Example 17, the subject matter of Example 16 may include, the request for the neurostimulation program being communicated to the programming guidance information system, the request including data that represents the physiological information and data that represents the therapy information, wherein the physiological information indicates one or more of: a medical condition, pain, or medical symptoms of the human subject, and wherein the therapy information indicates one or more of: a type of the neurostimulation device, a state of the neurostimulation device, respective locations for placements of leads of the neurostimulation device in the human subject, or a type of the leads and a number of the leads of the neurostimulation device in the human subject.

In Example 18, the subject matter of any one or more of Examples 16-17 may include, the plurality of programmable parameter settings including settings for one or more of: pulse patterns, pulse shapes, or a spatial location, of pulses of modulated energy provided with a plurality of leads of the neurostimulation device.

In Example 19, the subject matter of any one or more of Examples 16-18 may include, the plurality of programmable parameter settings including settings for two or more of: a frequency, a pulse width, a number of pulses within a burst or train of pulses, the train-to-train interval, the burst frequency of trains of pulses, a pulse duty cycle, or a burst duty cycle, of the pulses of modulated energy provided with a plurality of leads of the neurostimulation device.

In Example 20, the subject matter of any one or more of Examples 16-19 may include, the user interface processing circuitry to further perform electronic operations with the device to: receive, from the programming guidance information system, rating data and comment data for the neurostimulation program corresponding to the physiological information and the therapy information; and wherein the representation of the program data includes a representation of the rating data and the comment data in the graphical user interface, the representation to depict respective clinician ratings and comments provided for respective implementations of the neurostimulation program.

In Example 21, the subject matter of Example 20 may include, the representation of the program data including a listing of the neurostimulation program and a plurality of additional neurostimulation programs, the additional neurostimulation programs corresponding to the physiological information and the therapy information, and wherein the listing is ordered based on the respective clinician ratings and comments for the respective neurostimulation programs.

In Example 22, the subject matter of any one or more of Examples 16-21 may include, the programming guidance information system being accessible via a network connection, and wherein the programming guidance information system includes a data interface accessible via the network connection to receive the request for the neurostimulation program and transmit the program data of the neurostimulation program in response to the request, and wherein the programming guidance information system is operable to select the neurostimulation program from among a plurality of candidate neurostimulation programs represented in remote data storage accessible to the programming guidance information system.

In Example 23, the subject matter of Example 22 may include, the neurostimulation program being selected by the programming guidance information system based on a number of matches of a plurality of characteristics of the physiological information and the therapy information to characteristics of the neurostimulation program, and wherein the number of matches for the neurostimulation program exceeds a number of matches of the plurality of candidate neurostimulation programs with the plurality of characteristics for the physiological information and the therapy information.

In Example 24, the subject matter of any one or more of Examples 16-23 may include, the user interface processing circuitry to further perform electronic operations with the device to: receive, in the graphical user interface, a clinician input of a rating and a comment for an update to the neurostimulation program; transmit, to the programming guidance information system, updated program data for the update to the neurostimulation program; and transmit, to the programming guidance information system, data representing the rating and the comment for the update to the neurostimulation program; wherein the program data is used in an initial programming of the neurostimulation device, and wherein the update to the neurostimulation program is provided from clinician modification of one or more of the plurality of programmable parameter settings of the neurostimulation program.

In Example 25, the subject matter of any one or more of Examples 16-24 may include, the graphical user interface providing an input screen to receive the clinician input of the physiological information and the therapy information and an output screen to output the representation of the program data of the neurostimulation program.

In Example 26, the subject matter of any one or more of Examples 16-25 may include, the user interface processing circuitry to further perform electronic operations with the device to: transmit the plurality of programmable parameter settings to a programming device, the programming device to program the neurostimulator device using the plurality of programmable parameter settings.

Example 27 includes subject matter (such as a method, means for performing acts, machine readable medium including instructions that when performed by a machine cause the machine to performs acts, or an apparatus to perform), comprising a plurality of electronic operations executed with a processor and memory of a computer system, the plurality of electronic operations including: receiving, in a graphical user interface, a clinician input of physiological information and therapy information for neurostimulation treatment of a human subject using a neurostimulation device; requesting, from a programming guidance information system, a neurostimulation program corresponding to the physiological information and the therapy information; receiving, from the programming guidance information system, program data for the neurostimulation program corresponding to the physiological information and the therapy information, and outputting, in the graphical user interface, a representation of the program data of the neurostimulation program corresponding to the physiological information and the therapy information; wherein the neurostimulation program includes a plurality of programmable parameter settings for operational control of the neurostimulation device.

In Example 28, the subject matter of Example 27 may include, the request for the neurostimulation program being communicated to the programming guidance information system, the request including data that represents the physiological information and data that represents the therapy information, wherein the physiological information indicates one or more of: a medical condition, pain, or medical symptoms of the human subject, and wherein the therapy information indicates one or more of: a type of the neurostimulation device, a state of the neurostimulation device, respective locations for placements of leads of the neurostimulation device in the human subject, or a type of the leads and a number of the leads of the neurostimulation device in the human subject.

In Example 29, the subject matter of any one or more of Examples 27-28 may include, the plurality of programmable parameter settings including settings for one or more of: pulse patterns, pulse shapes, or a spatial location, of pulses of modulated energy provided with a plurality of leads of the neurostimulation device.

In Example 30, the subject matter of any one or more of Examples 27-29 may include, the electronic operations further including: receiving, from the programming guidance information system, rating data and comment data for the neurostimulation program corresponding to the physiological information and the therapy information; wherein the representation of the program data includes a representation of the rating data and the comment data in the graphical user interface, the representation to depict respective clinician ratings and comments provided for respective implementations of the neurostimulation program.

In Example 31, the subject matter of Example 30 may include, the representation of the program data including a listing of the neurostimulation program and a plurality of additional neurostimulation programs, the additional neurostimulation programs corresponding to the physiological information and the therapy information, and wherein the listing is ordered based on the respective clinician ratings and comments for the respective neurostimulation programs.

In Example 32, the subject matter of any one or more of Examples 27-31 may include, the programming guidance information system being accessible to the computer system via a network connection, and wherein the programming guidance information system includes a data interface accessible via the network connection to receive the request for the neurostimulation program and transmit the program data of the neurostimulation program to the computer system in response to the request, and wherein the neurostimulation program is selected by the programming guidance information system based on matching a plurality of characteristics of the physiological information and the therapy information to characteristics of the neurostimulation program.

In Example 33, the subject matter of any one or more of Examples 27-32 may include, the electronic operations further including: receiving, in the graphical user interface, a clinician input of a rating and a comment for an update to the neurostimulation program; transmitting, to the programming guidance information system, updated program data for the update to the neurostimulation program; and transmitting, to the programming guidance information system, data representing the rating and the comment for the update to the neurostimulation program; wherein the program data is used in an initial programming of the neurostimulation device, and wherein the update to the neurostimulation program is provided from clinician modification of one or more of the plurality of programmable parameter settings of the neurostimulation program.

In Example 34, the subject matter of any one or more of Examples 27-33 may include, the electronic operations further including: transmitting the plurality of programmable parameter settings to a programming device, the programming device to program the neurostimulator device using the plurality of programmable parameter settings.

Example 35 includes subject matter (such as a machine-readable medium) including instructions, which when executed by a machine, cause the machine to: receive, in a graphical user interface, a clinician input of physiological information and therapy information for neurostimulation treatment of a human subject using a neurostimulation device; request, from a programming guidance information system, a neurostimulation program corresponding to the physiological information and the therapy information; receive, from the programming guidance information system, program data for the neurostimulation program corresponding to the physiological information and the therapy information; and output, in the graphical user interface, a representation of the program data of the neurostimulation program corresponding to the physiological information and the therapy information; wherein the neurostimulation program includes a plurality of programmable parameter settings for operational control of the neurostimulation device.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 8 illustrates, by way of example, an embodiment of a graphical user interface of a clinician guidance system for selecting and reviewing programming parameters of a neurostimulation system.

DETAILED DESCRIPTION

Figure 1:
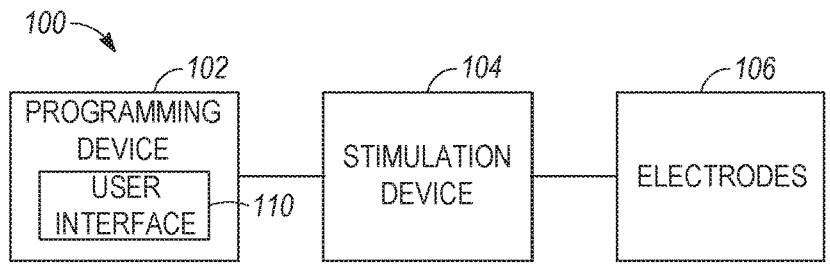
FIG. 1 illustrates, by way of example, an embodiment of a neurostimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document discusses various techniques that can allow a user to select and implement certain programming parameters (e.g., settings) for a neurostimulator, based on such programming parameters being arranged or defined into sets of neurostimulation programs (also plainly referred to as "programs" in this document). The techniques of this document can allow the user the ability to select a particular program from a plurality of available programs based on the desired characteristics of treatment, including initial treatment settings used as a starting or beginning "template" for treating a certain medical condition with the neurostimulation device. The various techniques are implemented through the use of user interfaces and application interfaces to access, select, retrieve, update, store, and persist programmable parameters of a program (or to implement a collection of such programmable parameters in a program). This can enable a clinical user such as a physician to more effectively program a neurostimulator with a known collection of predefined settings, particularly when initially deploying or reprogramming the neurostimulator device.

The system described in this disclosure allows a clinical user to select, view, and implement a particular neurostimulation program based on characteristics specific to the deployment of the neurostimulation device in a human subject, including physiological information (e.g., characteristics of pain and other medical symptoms of the human subject), therapy information (e.g., locations, types, and numbers of leads of the neurostimulator), and like information that is relevant to the medical treatment of the human subject. The neurostimulation program that is accessed and output with the interfaces of the present disclosure can implement control for a variety of parameters of operation of the neurostimulation device. By way of example, such parameters may include amplitude, frequency, pulse width, patterns of neurostimulation pulses, waveforms in the patterns of pulses, and like settings with respect to neurostimulator output on individual or a plurality of respective leads. The neurostimulator may use current or voltage sources to provide the neurostimulator output. The combination of settings are achieved by a user interface (e.g., a graphical user interface (GUI)) that enables a clinical user to select and obtain a program, including a plurality of recommended programmable parameter settings, for operational control of the neurostimulation device. The features of this user interface, discussed in additional detail, enable a more precise and focused identification of a corresponding program and effective use of a neurostimulator program treatment, based on data values that indicate the specific and unique physiological and deployment characteristics of the neurostimulator deployment for the human subject.

In various embodiments, a neurostimulator program may include parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use. As a result, the present techniques may be used as a starting, initial, default, experimental, recommended, or subsequent programming setting when implementing and selecting a program for a human subject in clinical setting.

In various embodiments, the present subject matter may be implemented using a combination of hardware and software designed to provide users such as clinical researchers, physicians or other caregivers with the ability to select and implement programs including defined waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other forms of energy.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a clinical user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical user interface) that allows the user to set and/or adjust values of the user-programmable parameters by creating, editing, loading, and removing programs that include parameter combinations such as patterns and waveforms, or changing and editing values for the user-programmable parameters or sets of the user-programmable parameters individually. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

As described in more detail below with respect to FIGS. 6 and 7, the user, e.g., clinical researcher or physician, can load and implement one or more parameters using all or portions of defined program, e.g., that was a result of neurostimulation research or previously deployed in another human subject. Based on received user input and the selected program, the programming device 102 can determine a subset of available electrodes and current distributions for the subset to generate the stimulation output. Example parameters that can be implemented by a program and are modifiable by received user input include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). The user input can be received in a clinical guidance user interface or in the user interface 110 of the programming device 102. This user input can implement or modify a program that specifies one or more of these parameters to define at least one of a pulse of the neurostimulation waveform, a pulse group of the neurostimulation waveform, and a group of pulse groups of the neurostimulation waveform, for example; the user input can also specify customized values for one or more of these parameters.

Figure 6:
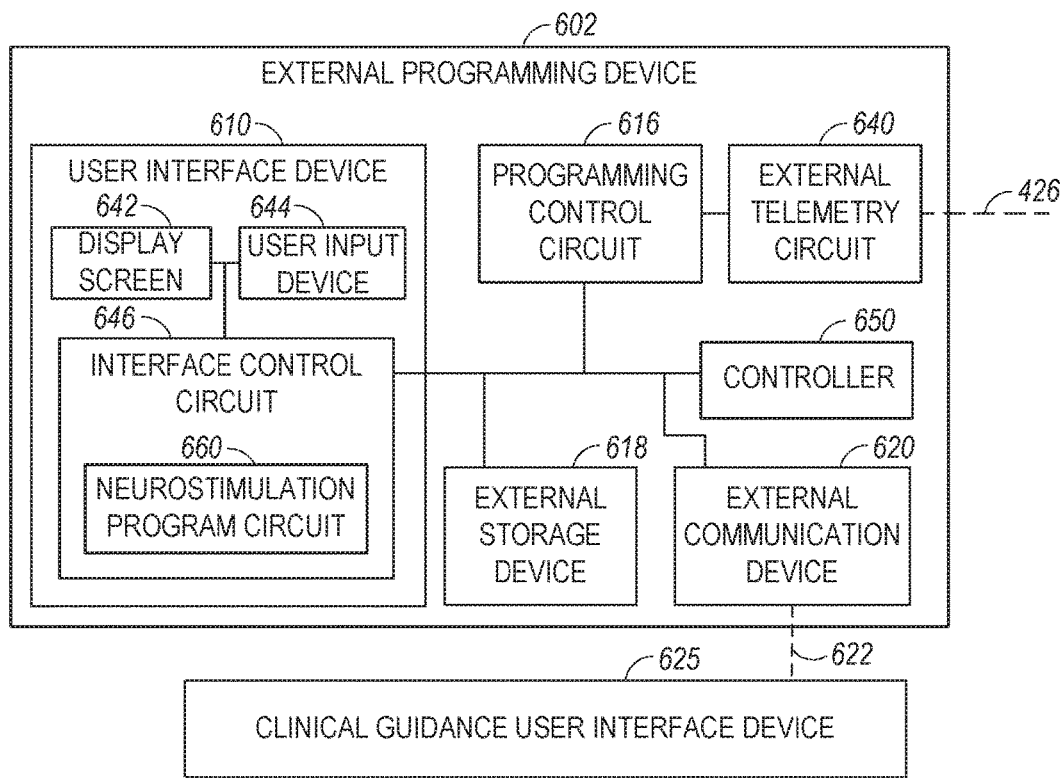
FIG. 6 illustrates, by way of example, an embodiment of a clinical guidance user interface device and an external programming device for a neurostimulation system, such as the implantable neurostimulation system of FIG. 4.

A controller, e.g., controller 650 of FIG. 6, can retrieve from a storage device, e.g., external storage device 618 of FIG. 6, or via an external communication device 620 of FIG. 6 from a clinical guidance user interface device 625, corresponding program(s) and parameter(s) that implement a specific neurostimulation waveform, a specific pulse group, a specific group of pulse groups, and the like. As also described in more detail below with respect to FIG. 6 and thereafter, in some example implementations, the user can obtain a recommended, matching, or corresponding program of parameters from a clinical guidance user interface device 625 that is selected for use with the stimulation device 104. This guided program of parameters may be selected and implemented with the programming device 102 as a "best match" for initial or updated programming settings of the stimulation device 104, to address the specific medical treatment and treatment objectives for a human subject.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could include a subcutaneous medical device (e.g., subcutaneous ICD, subcutaneous diagnostic device), wearable medical devices (e.g., patch based sensing device), or other external medical devices.

Figure 2:
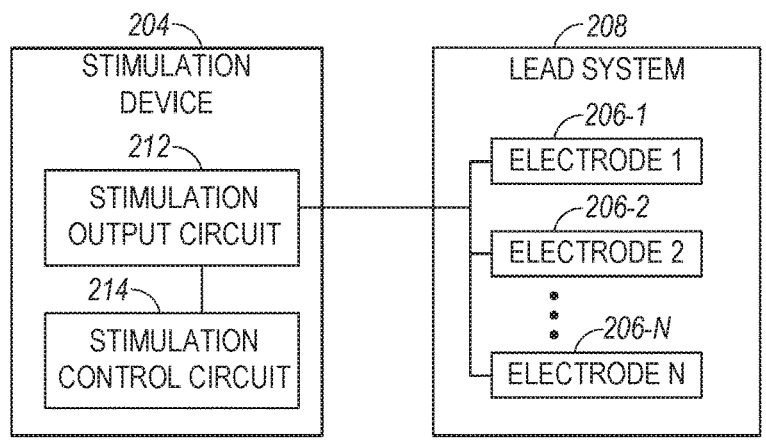
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry and power.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, SCS systems may have as many as thirty-two electrodes which exponentially increases the number of modulation parameter value combinations available for programming. To facilitate such programming, the clinician generally programs and modifies the modulation parameters through a computerized programming system, to allow the optimum modulation parameters to be determined based on patient and clinician feedback. However, the identification of starting modulation parameters is often limited to a clinician's personal knowledge of the device capabilities, followed by a time consuming adjustments and reprogramming for the modulation parameters. Thus, although patient or clinician feedback reflecting pain, paresthesia coverage, or other aspects of patient satisfaction with the stimulation may guide adjustments and changes to parameter settings, the initial settings and programming of the neurostimulator is quite limited with existing techniques. The implementation and use of the clinical guidance user interface as described further in FIG. 6 and thereafter provides a mechanism to obtain initial parameter settings and adjustment recommendations to implemented parameter settings, based on the specific physiological information and therapy information for the neurostimulator deployment.

Figure 3:
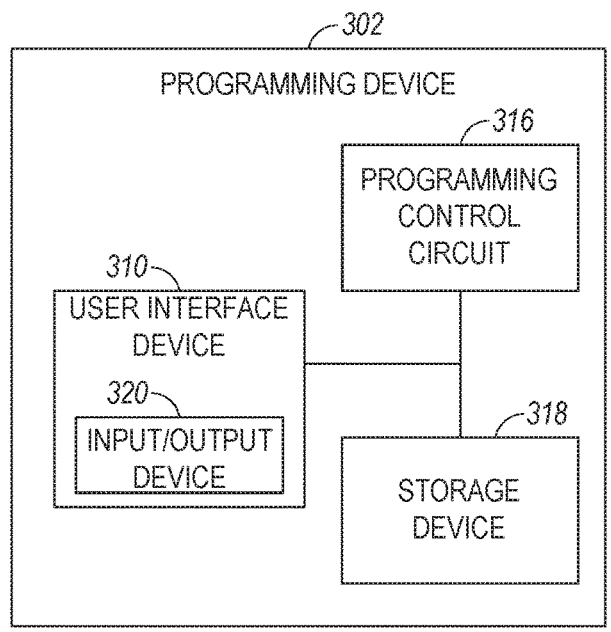
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), including values of a therapeutic neurostimulation field. In some examples, the user interface device 310 can receive user input to initiate the implementation of the programs which are recommended or loadable through various clinically guided user interfaces, which are described in more detail below.

In various embodiments, the input/output device 320 allows the clinical user to apply, change, or modify certain building blocks and a frequency at which the program is delivered. In various embodiments, the input/output device 320 can allow the user to save, retrieve, and modify programs loaded from the clinical guidance user interface and stored in storage device 318 as templates. In various embodiments, the input/output device 320 and accompanying software on the user interface device 310 allows each newly created building blocks, program components, programs, and program modifications to be saved, stored, or otherwise persisted in storage device 318.

In one embodiment, the input/output device 320 includes a touchscreen. In various embodiments, the input/output device 320 includes any type of presentation device, such as interactive or non-interactive screens, and any type of user input device that allows the user to interact with a user interface to edit or modify waveforms, building blocks, and program components, and to implement, remove, or schedule the programs. Thus, the input/output device 320 may include one or more of a touchscreen, keyboard, keypad, touchpad, trackball, joystick, and mouse. In various embodiments, circuits of the neurostimulation system 100, including its various embodiments discussed in this document, may be implemented using a combination of hardware and software. For example, the logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
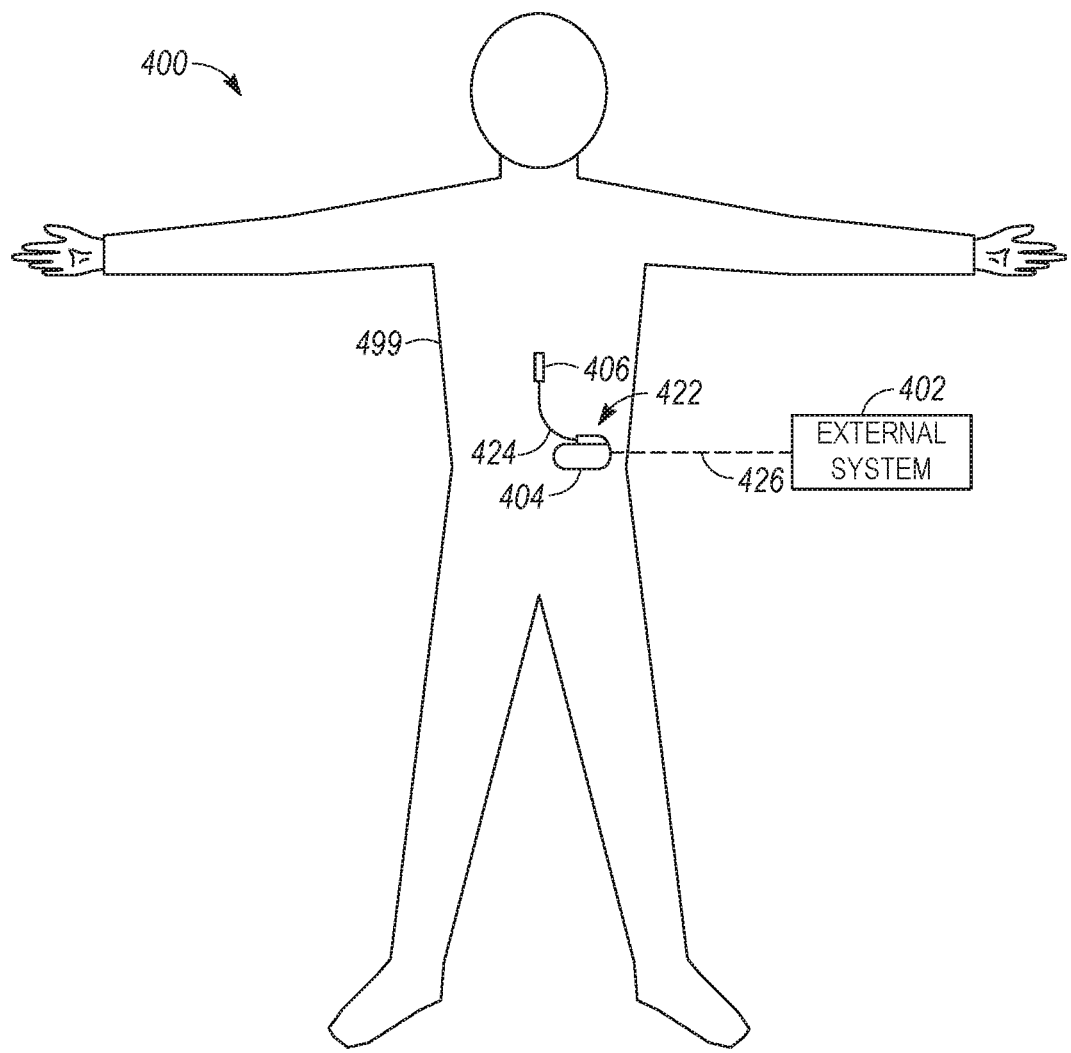
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism for the patient to provide feedback on the operation of the implantable neuromodulation system. Feedback may be metrics reflecting perceived pain, effectiveness of therapies, or other aspects of patient comfort or condition.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. It will be understood that other clinical effects and physiological mechanisms may also be provided through use of such stimulation techniques.

Figure 5:
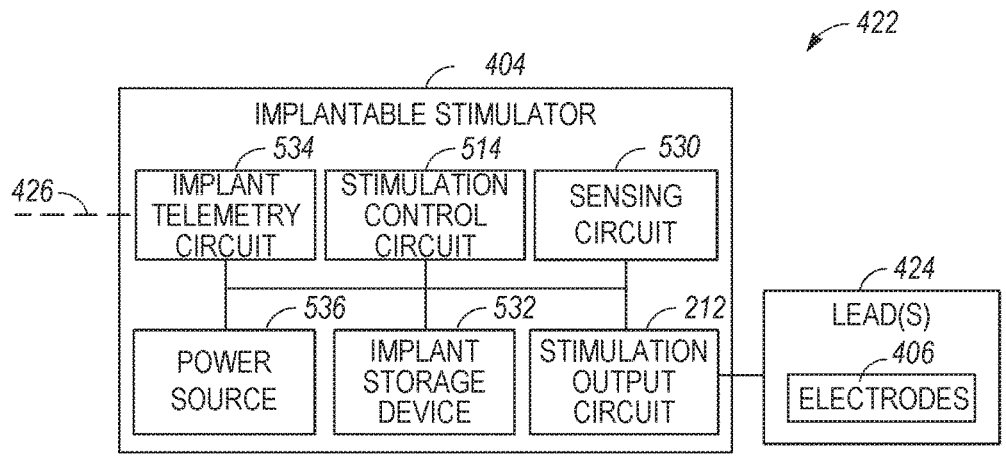
FIG. 5 illustrates, by way of example, an embodiment of an implantable stimulator and one or more leads of a neurostimulation system, such as the implantable neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program obtained from a clinical guidance user interface) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs obtained using the clinical guidance techniques disclosed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530 (if included), the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of an external programming device 602 of an implantable neurostimulation system, such as the external system 402. The external programming device 602 represents an embodiment of the programming device 302, and includes an external telemetry circuit 640, an external storage device 618, a programming control circuit 616, a user interface device 610, a controller 650, and an external communication device 620.

External telemetry circuit 640 provides the external programming device 602 with wireless communication with another controllable device such as the implantable stimulator 404 via the telemetry link 426, including transmitting the plurality of stimulation parameters to the implantable stimulator 404. In one embodiment, the external telemetry circuit 640 also transmits power to the implantable stimulator 404 through inductive coupling.

External communication device 620 provides a mechanism to conduct communications with a clinical guidance user interface device 625 via an external communication link 622. As described in the following disclosure, the clinical guidance user interface device 625 may provide data to the external programming device 602 that corresponds to a neurostimulation program or characteristics of a neurostimulation program. The clinical guidance user interface device 625 may also receive data from the external programming device 602 that indicates previous characteristics of programming or treatment, including medical characteristics unique to the patient. The external communication device 620 and the clinical guidance user interface device 625 may communicate using any number of wired or wireless communication mechanisms described in this document, including but not limited to an IEEE 802.11 (Wi-Fi), Bluetooth, Infrared, and like standardized and proprietary wireless communications implementations. Although the external telemetry circuit 640 and the external communication device 620 are depicted as separate components within the external programming device 602, the functionality of both of these components may be integrated into a single communication chipset, circuitry, or device.

External storage device 618 stores a plurality of existing neurostimulation waveforms, including definable waveforms for use as a portion of the pattern of the neurostimulation pulses, and other portions of a program. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, electrode configurations, total charge injected per unit time, cycling (e.g., on/off time), pulse shape, number of phases, phase order, interphase time, charge balance, and ramping.

The external storage device 618 also stores a plurality of individually definable fields which may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes.

The programming control circuit 616 represents an embodiment of a programming control circuit 316 and generates the plurality of stimulation parameters, which is to be transmitted to the implantable stimulator 404, based on the pattern of the neurostimulation pulses. The pattern is defined using one or more waveforms selected from the plurality of individually definable waveforms (e.g., defined by a program) stored in an external storage device 618. In various embodiments, a programming control circuit 616 checks values of the plurality of stimulation parameters against safety rules to limit these values within constraints of the safety rules. In one embodiment, the safety rules are heuristic rules.

The user interface device 610 represents an embodiment of the user interface device 310 and allows the user to select, modify, or otherwise define the pattern of neurostimulation pulses and perform various other monitoring and programming tasks. The user interface device 610 can enable a user to implement a program including the program or program parameters recommended or indicated by the clinical guidance user interface device 625. The user interface device 610 includes a display screen 642, a user input device 644, and an interface control circuit 646. The display screen 642 may include any type of interactive or non-interactive screens, and the user input device 644 may include any type of user input devices that supports the various functions discussed in this document, such as touchscreen, keyboard, keypad, touchpad, trackball, joystick, and mouse. In one embodiment, the user interface device 610 includes an interactive screen that displays a graphical representation of one or more stimulation waveforms associated with a program or program parameters recommended or indicated by the clinical guidance user interface device 625. In a further embodiment, the user interface device 610 and allows the user to adjust the waveform (or other aspects of the program or program parameters) by graphically editing the waveform and/or various building blocks of the waveform, or by modifying other aspects of the program or program parameters obtained from the clinical guidance user interface device 625. The user interface device 610 may also allow the user to perform any other functions discussed in this document where graphical editing is suitable as may be appreciated by those skilled in the art.

Interface control circuit 646 controls the operation of the user interface device 610 including responding to various inputs received by the user input device 644 that define or modify characteristics of implementation (including conditions, schedules, and variations) of one or more programs, parameters within the program, characteristics of one or more stimulation waveforms within a program, and like neurostimulator operational values that may be obtained from the clinical guidance user interface device 625. Interface control circuit 646 includes neurostimulation program circuit 660 may generate a visualization of such characteristics of implementation, and receive and implement commands to implement the program and the neurostimulator operational values. These commands and visualization may be performed in a review and guidance mode, or in a real-time programming mode. For example, in a real-time programming mode, the programming control circuit 616 dynamically updates values of the plurality of stimulation parameters in response to user input with the user interface device 610 such as implementation of a selected program received from the clinical guidance user interface device 625, and the programming control circuit 616 accordingly transmits the plurality of stimulation parameters with the updated values defined by the selected program to the implantable stimulator 404.

The controller 650 can be a microprocessor that communicates with the external telemetry circuit 640, the external communication device 620, the external storage device 618, the programming control circuit 616, and the user interface device 610, via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor.

In accordance with various techniques of this disclosure, the controller 650 can receive, via the user interface device 610 for example, user input that at least partially defines implementation characteristics of a recommended neurostimulation program to provide therapy to a patient. This recommended neurostimulation program may be received or obtained from the clinical guidance user interface device 625. After having received the user input, the controller 650 can execute instructions that cause the programming control circuit 616 to generate a plurality of stimulation parameters to generate the neurostimulation field in accordance with the recommended neurostimulation program (and any changes to the neurostimulation program provided by the clinician). In particular, the programming control circuit 316 can determine a subset of electrodes from the number of available electrodes on the lead(s), and current distributions associated with electrodes in the subset (including various pulses and waveforms defined by the recommended neurostimulation program).

Using the example techniques of this disclosure, using the external programming device 602 and the clinical guidance user interface device 625, a series of user interfaces may provide guidance and recommended parameter settings to clinicians. For example, in example implementations, the clinical guidance user interface device 625 may be used to receive clinician input of physiological information and therapy information for treatment of a particular human subject. This clinical guidance user interface device 625 may access a remote data service (further referred to as a "programming guidance information system") to obtain a recommended program and program data based on this physiological and therapy information. In response, the clinical guidance user interface device may provide a mechanism to transfer settings of the recommended program or program data to the external programming device 602, such as with use of the external communication link 622. The external programming device 602 can receive a further user selection or modification to the program, e.g., using the user interface device 610, which allows a user to select and adjust specific parameter settings of the program.

As also discussed in the following examples, using the clinical guidance user interface device 625, a series of user interfaces may allow clinicians to share settings with other, and rate combinations of settings, in order to enable clinicians to obtain and choose therapeutic settings. These user interfaces may interface with a network-based (e.g., cloud-based) system allowing the storage, retrieval, and access of parameter settings, including additional information about such settings. This additional information may include clinician ratings, feedback, comments, or the like, for such parameter and program settings. The network-based system may also be used in a closed social network to connect clinicians with other profiles of clinicians who are performing similar treatments.

As will be understood, the variety of settings for a neurostimulation device may be provided by many variations of programming parameter settings. Existing programmers provide the flexibility to the clinicians to program stimulators using a wide variety of programming parameters. Thus, an inordinately large number of such program parameter combinations exist. Often a clinician is expected to determine out a specific set of parameter combinations that works best for patients based on his or her personal experience and trial and error, to arrive at a usable setting for a particular patient. The following system and methods provide applied mechanisms to better tailor the programming of parameter combinations to particular therapies depending on the treatment type, symptoms, and clinical objectives. These parameter combinations may be selected as a template of settings in a program, a macro-based or automated implementation of settings in a program, recommended or suggested adjustments or modifications to an existing program, and like variations.

In one example, the clinical guidance user interface device 625 may be provided in the form factor of a software application interface (e.g., "mobile app") natively operating on a mobile device such as a smartphone or tablet. In another example, the clinical guidance user interface device 625 may be provided in the form factor of a network-based application interface (e.g., "browser") operating on a computing device such as a desktop or notebook computer, a smartphone or tablet, or the like. In another example, the clinical guidance user interface device 625 may be provided in the form of a native software application that is installed, programmed, or customized to the hardware characteristics of a subject computing device. It will be understood from the following description, however, that the deployment of the user interface in a mobile app or browser-based format may provide enhanced portability and accessibility of the user interface.

Figure 7:
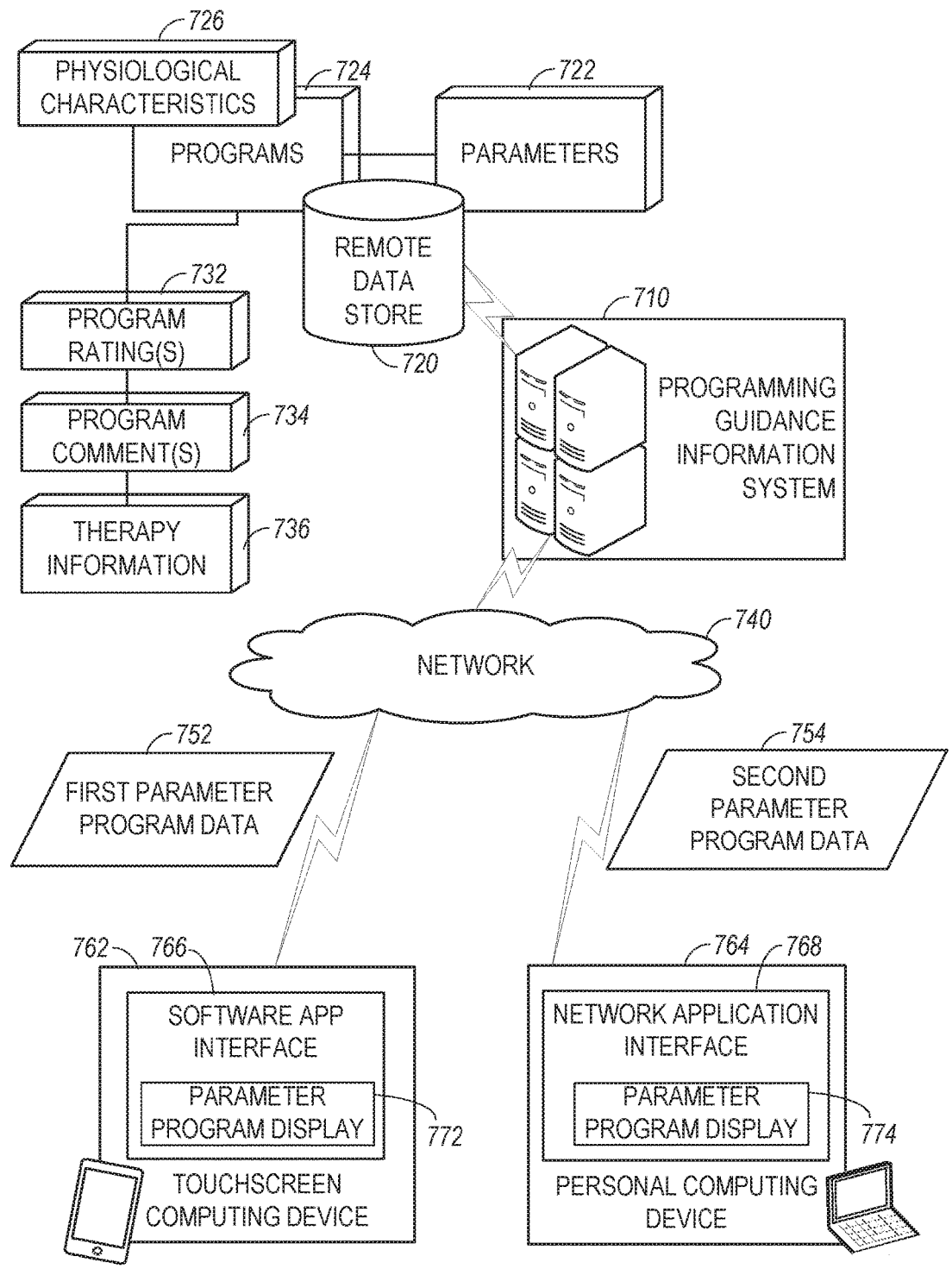
FIG. 7 illustrates, by way of example, an embodiment of data interactions between a programming guidance information system and embodiments of a clinical guidance user interface device for communicating programming parameters of a neurostimulation system.

FIG. 7 illustrates, by way of example, an embodiment of data interactions between a programming guidance information system and embodiments of a clinical guidance user interface device (e.g., the clinical guidance user interface device 625) for communicating programming parameters of a neurostimulation system. The clinical guidance user interface device is shown in FIG. 7 in the form of a touchscreen computing device 762 (e.g., a smartphone or tablet) and a personal computing device 764 (e.g., a notebook or desktop PC), with the touchscreen computing device 762 being specially programmed to operate a first clinical guidance user interface (in a software app interface 766) and with the personal computing device 764 being specially programmed to operate a second clinical guidance user interface (in a network application interface 768, e.g., a browser). It will be understood that other form factors and embodiments of the clinical guidance user interface device, including the use of network appliances or the integration of the clinical guidance user interface device into external programming devices or circuitry, may also be implemented.

The clinical guidance user interface device (e.g., the touchscreen computing device 762 and the personal computing device 764) may each communicate to a programming guidance information system 710 via a network 740 (e.g., a private local area network, public wide area network, the Internet, and the like). The programming guidance information system 710 serves as a data service that hosts program information for a plurality of neurostimulation programs across multiple facilities or facility locations. In an example, the programming guidance information system 710 may be operated or hosted by a research institution or a medical device provider (e.g., a manufacturer of the neurostimulation device) for collecting data among a plurality of clinical deployments. The programming guidance information system 710 may operate as a middleware layer of a larger information system, serving as an interface to backend components such as additional data servers, databases, including the remote data store 720 discussed herein.

The respective user interfaces (the software app interface 766 and the network application interface 768) are configured to access or generate one or more recommendations for the programming parameters and programs, using a remote database of program settings accessed via a network by the user interface. For example, this remote database of programming settings may reside at a cloud-hosted service used to connect a plurality of connected devices and clinicians. This database, which may be hosted by the programming guidance information system 710, may be accessed using an application programming interface (API) or other remotely accessible interface of the programming guidance information system 710.

The software app interface 766 and the network application interface 768 may include a respective parameter program display 772, 774 to output the one or more recommendations for available parameters and programs, along with accompanying ratings, reviews, comments and notes. These parameter settings may be accessible in the form of individual programming values that can be accessed, viewed, and observed as part of modifiable device setting or group of settings; the parameter settings may also be provided as part of a program and program data.

The programming guidance information system 710 operates to provide program data upon request to a clinical guidance user interface device, such as with first parameter program data 752 that is transmitted to the touchscreen computing device 762 and with second parameter program data 754 that is transmitted to the personal computing device 764. The programming guidance information system 710 may provide the first parameter program data 752 in response to specific characteristics for treatment, such as physiological information and therapy information of a first patient; the programming guidance information system 710 may provide the second parameter program data 754 in response to other characteristics for treatment, such as physiological information and therapy information of a second patient. The programming guidance information system 710 may provide this program data on the basis of a "best match" of a plurality of characteristics, matched between the characteristics of a stored program and the characteristics of treatment for the particular patient. The programming guidance information system 710 may also provide multiple sets of program data, in the form of "candidate" programs for implementation, which allow a selection from among multiple "matching" characteristics. In a further example, the programming guidance information system 710 may provide a ranking of available programs within a listing of multiple candidate neurostimulation programs.

The remote data store 720 is used by the programming guidance information system 710 to establish and maintain a repository of available programs (e.g., programs 724) and parameter settings (e.g., parameters 722) for access, selection, and retrieval from an external interface of the programming guidance information system 710. The programs 724 that are represented in data in the remote data store 720 may respectively correspond to a plurality of the parameters 722 represented in data, including as many as hundreds or thousands of individual data values (e.g., programmable settings) relating to parameter combinations of a neurostimulation program. The programs 724 that are represented in data in the remote data store 720 may also respectively correspond to a plurality of physiological characteristics 726 that are represented in data for deployed neurostimulation treatments.

Additionally, the programs 724 that are represented in data in the remote data store 720 may be associated with one or more program ratings 732 (e.g., clinician ratings on a numerical scale), one or more program comments 734 (e.g., clinician textual comments and notes), and therapy information 736 (e.g., clinician observations or medical records for the neurostimulation device). The program ratings 732 may be provided from objective measured clinical feedback and responses to the implementation of specific neurostimulation programs, such as numerical ratings of efficacy for treating a particular pain condition. The program comments 734 may be provided from subjective measured clinical feedback and responses to implementation of specific neurostimulation programs, such as instructions or comments entered by a clinician or patient that relate to efficacy of treating a particular pain condition. The therapy information 736 may provide an indication of what types of treatments and neurostimulation procedures were applied to obtain the program rating 732 and the program comments 734 for the specific program deployment, such as the type of neurostimulation device, the state of the neurostimulation device, locations for placements of leads of the neurostimulation device, and the types and number of leads for the neurostimulation device. Accordingly, the programming guidance information system 710 may be used to obtain a "best match" not only on the basis of a program rating 732 for a treatment of a certain pain symptom (identified from the physiological characteristics 726), but also on the basis of identifying the type of device, location of electrode implantation, types of programs and protocols used, and other characteristics of a neurostimulation device procedure (identified from the therapy information 736).

A variety of data relationships, associations, and correlations may be established among the programs 724 and the characteristics 726, 732, 734, 736 in the remote data store 720. These relationships, associations, and correlations may be established with the use of algorithms, machine learning techniques, search strategies, and the like, to identify programs and program settings in response to a request or an input from the clinical guidance user interface. In a further example, particular programs may be selected, preferred, or ranked higher, on the basis of a common type of medical procedure or treatment, common type of medical facility or medical practice, social network connections between facilities, doctors, and other identifiable characteristics of a program that can be identified by programmable logic and algorithms.

Returning to the application interfaces provided by the software app interface 766 and the network application interface 768, such application interfaces may provide inputs to receive clinician input of characteristics, including physiological information and therapy information, for use with the programming guidance information system 710. Thus, the logic for the selection of a recommended program and like clinician guidance may be implemented at a remote information system. In response to the retrieval or selection of the recommended program (and other candidate programs, as applicable) in the clinical guidance user interface, the clinical guidance user interface may provide an output of the representation of the program data of the neurostimulation program that is a candidate for programming.

FIG. 8 illustrates, by way of example, an embodiment of a graphical user interface 800 of a clinician guidance system for selecting and reviewing programming parameters of a neurostimulation system. For example, the graphical user interface 800 may embody the characteristics of the parameter program display 772, 774 and other features of the respective user interfaces.

The graphical user interface 800 includes one or more inputs to receive physiologic information 810 and therapy information 820 for a neurostimulator device deployment. The graphical user interface 800 may be operated by a clinician (such as a company representative, a physician, or the like) who oversees or participates in the surgical planning or initial programming of the neurostimulation device.

The graphical user interface 800 includes input fields to receive information regarding physiological characteristics of the patient being considered for treatment, which may be entered in advance of, during, or after a surgery or other implantation procedure. For example, the physiological information 810 may receive an input of the nature of pain, location of pain, intensity of pain, spread of pain, or other physiological characteristics. The therapy information 820 may receive an input of the type or model of the neurostimulation device, the number of leads deployed from the device, electrode placement location, and like characteristics relevant to the therapy to be performed with the device. The inputs of the physiological information 810 and the therapy information 820 may be received using a variety of user interface controls, such as input boxes, drop-downs, graphical selection screens, and the like.

The graphical user interface 800 can include outputs for information corresponding to a selectable program. For example, a listing of available programs 830 may include an ordered list of candidate programs that are obtained from a library of programs (such as obtained from a remote programming guidance information system interface). The listing of available programs 830 may include, for example, a representation of a first program 840a and a representation of a second program 840b, with each representation including information on the program such as a relevancy rating (based on a match to the physiological information, therapy information), indications for treatment, device placement characteristics, clinician rating, and clinician comments. The representation of a first program 840a and the representation of a second program 840b may include respective selectable options to load the program 850a, 850b, such as to load the program in an external programmer device.

The graphical user interface 800 may also provide a user with features to sort, order, or organize a number of the candidate programs (e.g., in the listing of available programs 830) according to any number of measurements or preferences, such as characteristics of a treatment protocol or efficacy of treatment protocol. It will be understood that a variety of other inputs and outputs may be provided for user interaction in the graphical user interface 800 or other embodiments of the clinical guidance user interface.

Figure 9:
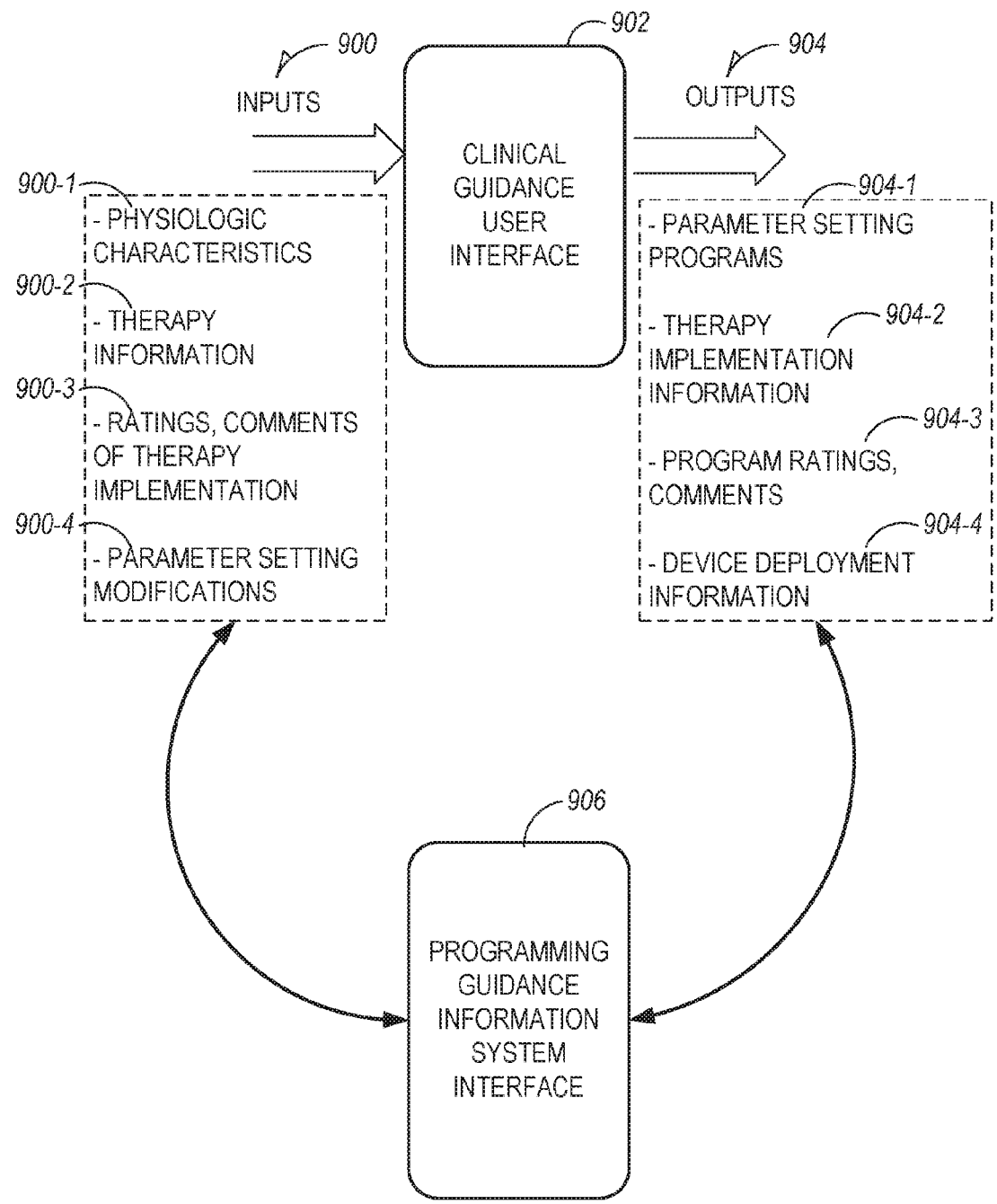
FIG. 9 illustrates, by way of example, an embodiment of a data and control flow in interaction with a programming guidance information system interface and clinical guidance user interface that communicate data to access programming parameters of a neurostimulation system.

FIG. 9 illustrates, by way of example, an embodiment of a data and control flow in interaction with a programming guidance information system interface and clinical guidance user interface that communicate data to access programming parameters of a neurostimulation system. As illustrated, the data and control flow may include a plurality of inputs 900 that are provided to a clinical guidance user interface 902, and a plurality of outputs 904 provided from the clinical guidance user interface 902.

The inputs that can be provided to the clinical guidance user interface 902 as part of a program selection or recommendation process (e.g., to obtain an initial program) may include measurements and indications of physiologic characteristics 900-1, relevant to the medical condition of the patient, and therapy characteristics 900-2, relevant to the neurostimulation treatment attributes applied (or to be applied) to the patient. The physiologic characteristics 900-1 may include information to represent the nature, location, intensity and spread of pain. The physiologic characteristics 900-1 may include information to represent other medical symptoms and statuses relevant to the patient and the medical condition. The therapy information 900-2 may include information that indicates a type of the neurostimulation device, a state of the neurostimulation device, respective locations for placements of leads, a type of the leads, or a number of the leads of the neurostimulation device in the human subject (such as from information obtained from an external programming device). The therapy information 900-2 may include information to represent other aspects of control and implementation variations for the neurostimulation device.

The use of the clinical guidance user interface 902 can assist clinicians with a determination of which program parameters are most suitable or beneficial for initial use in the neurostimulation device. This may be assisted through the plurality of outputs 904 using information obtained from the programming guidance information system interface 906. For example, the programming guidance information system 906 may provide data for the outputs 904 via the clinical guidance user interface 902, including the selection of parameter setting programs 904-1, therapy implementation information 904-2, and ratings and comments on respective programs 904-3.

The use of the clinical guidance user interface can also assist clinicians with a determination of which program parameters are most suitable or beneficial for modification or change in the neurostimulation device. Thus, although program settings may provide a starting point, further modification may be useful to assist variation attributable to the patient. The use of the clinical guidance user interface may assist the use and propagation of such modified settings, through the communication of modified program settings to the programming guidance information system 906 for use in other neurostimulation device deployments.

The clinical guidance user interface 902 may receive an input of a new or modified program, in the form of parameter setting modifications 900-4 (e.g., modifications to an initial program), that may be communicated to the programming guidance information system interface 906. Additionally, the clinical guidance user interface 902 may provide the output of ratings and comments of a neurostimulation program implementation (such as an updated program that implements the parameter setting modifications 900-4). In an example, the physiologic information that is stored, communicated, or maintained by either interface 902, 906 may be anonymized or non-sensitive data (e.g., data that does not include protected health information from an identifiable patient). In another example, the software or the programming guidance information system interface 906 may perform operations to anonymize or genericize patient-identifiable data values.

In further examples, the clinical guidance user interface 902 may provide device deployment information 904-4 to assist surgical or medical operations of the neurostimulator, such as an indication of locations for the placement of respective electrodes to perform a particular program. Thus, the outputs 904 of the clinical guidance user interface 902 may include surgical or medical procedure information to be used by the clinician during an installation or adjustment of the neurostimulation device. Further information from the outputs 904 of the clinical guidance user interface may also include safety guidance, recommendations, warnings, and like information related to the use of specific programs or types of treatment(s).

Figure 10:
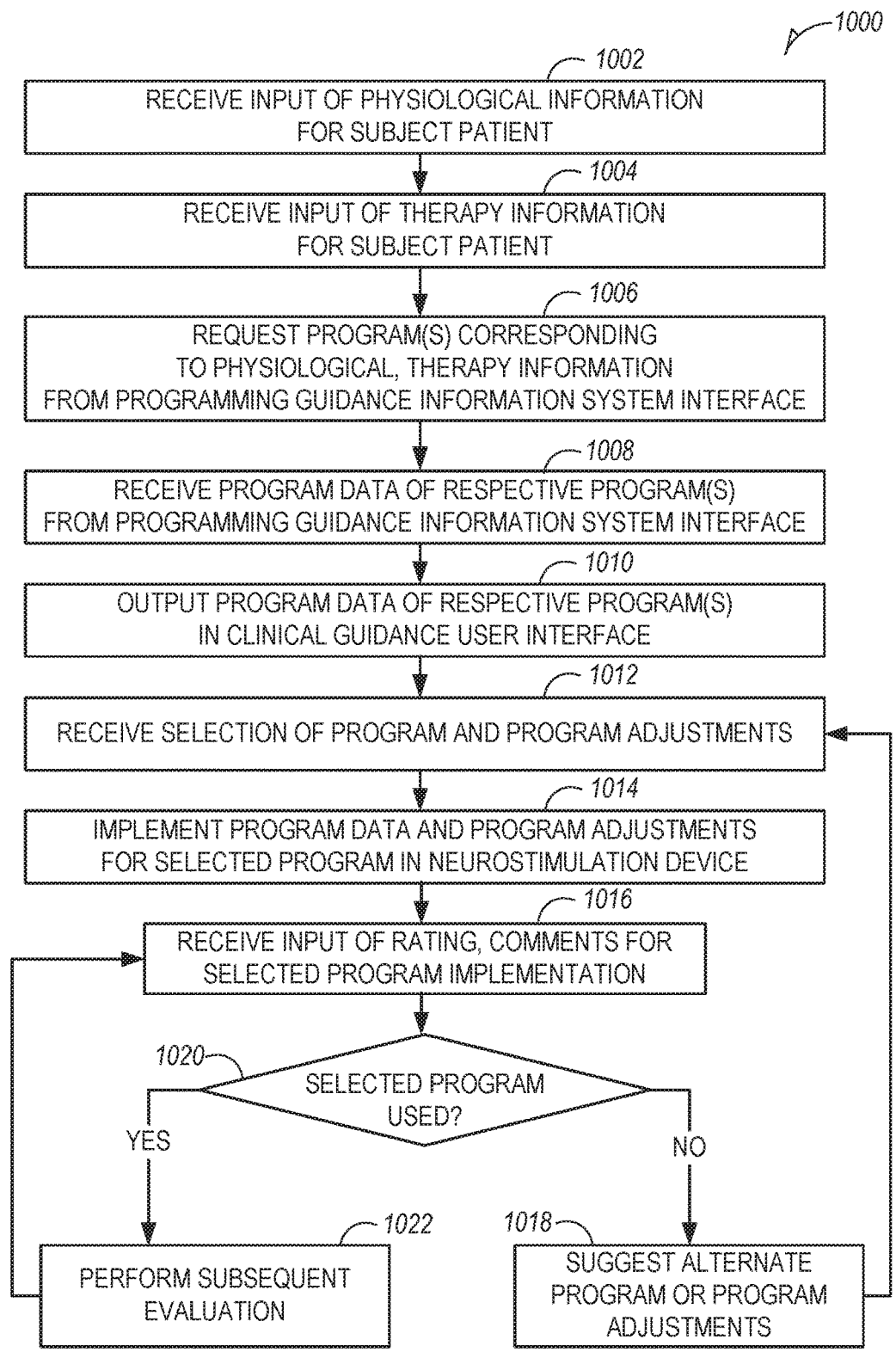
FIG. 10 illustrates, by way of example, an embodiment of a method implemented by a clinical guidance user interface device for accessing and providing a program of parameters for a neurostimulation device.

FIG. 10 illustrates, by way of example, an embodiment of a method 1000 implemented by a clinical guidance user interface device for accessing and providing a program of parameters for a neurostimulation device. This method 1000 may be implemented with use of electronic operations within a clinical guidance user interface, such as interfaces 766, 768, 800, and 902 discussed above.

For example, the clinical guidance user interface operates to receive input of treatment-based information for a subject patient, including the input of physiological information (operation 1002) such as data that indicates a medical condition of the human subject and data that indicates pain and medical symptoms of the human subject, and therapy information (operation 1004), such as data that indicates a type of the neurostimulation device, data that indicates a state of the neurostimulation device, data that indicates respective locations for placements of leads of the neurostimulation device in the human subject, or data that indicates a type of the leads and a number of the leads of the neurostimulation device in the human subject. In response to this input or a user command received in the clinical guidance user interface, the clinical guidance user interface operates to request candidate programs, from a programming guidance information system interface, for candidate programs that correspond to the physiological and therapy information (operation 1006).

The clinical guidance user interface subsequently receives program data, from the programming guidance information system interface, of respective candidate programs that correspond to the physiological and therapy information (operation 1008). The clinical guidance user interface then parses this information, and provides a data representation of the candidate programs in the clinical guidance user interface (operation 1010). This data representation may include a listing of candidate programs, including accompanying rating and comment information for respective programs.

The clinical guidance user interface, or a coupled user interface for a programming device, then receives a selection of a particular program (and program adjustments, as applicable) for deployment of a selected program in a neurostimulation device (operation 1012). The program data (and program adjustments to the selected program) are then implemented in the neurostimulation device (operation 1014), such as with use of an external programmer device. Based on the results of the neurostimulation treatment, further adjustments and changes to the program implementation may occur (repeating operations 1012, 1014). Based on the results of the neurostimulation treatment from the selected program implementation, the clinical guidance user interface may operate to receive a rating and comments for a selected program implementation (operation 1016). If the selected program is deployed in the neurostimulation device for a duration of time (evaluation 1020), then a subsequent evaluation of the user may be performed to obtain follow-on ratings and comments (operation 1022). If the selected program is not deployed in the neurostimulation device for a duration of time (evaluation 1020), then the clinical guidance user interface may operate to provide recommendations or suggestions of an alternate program or program adjustments (operation 1018), and guide the user towards selection of the alternate program or program adjustment (returning to operation 1012).

Figure 11:
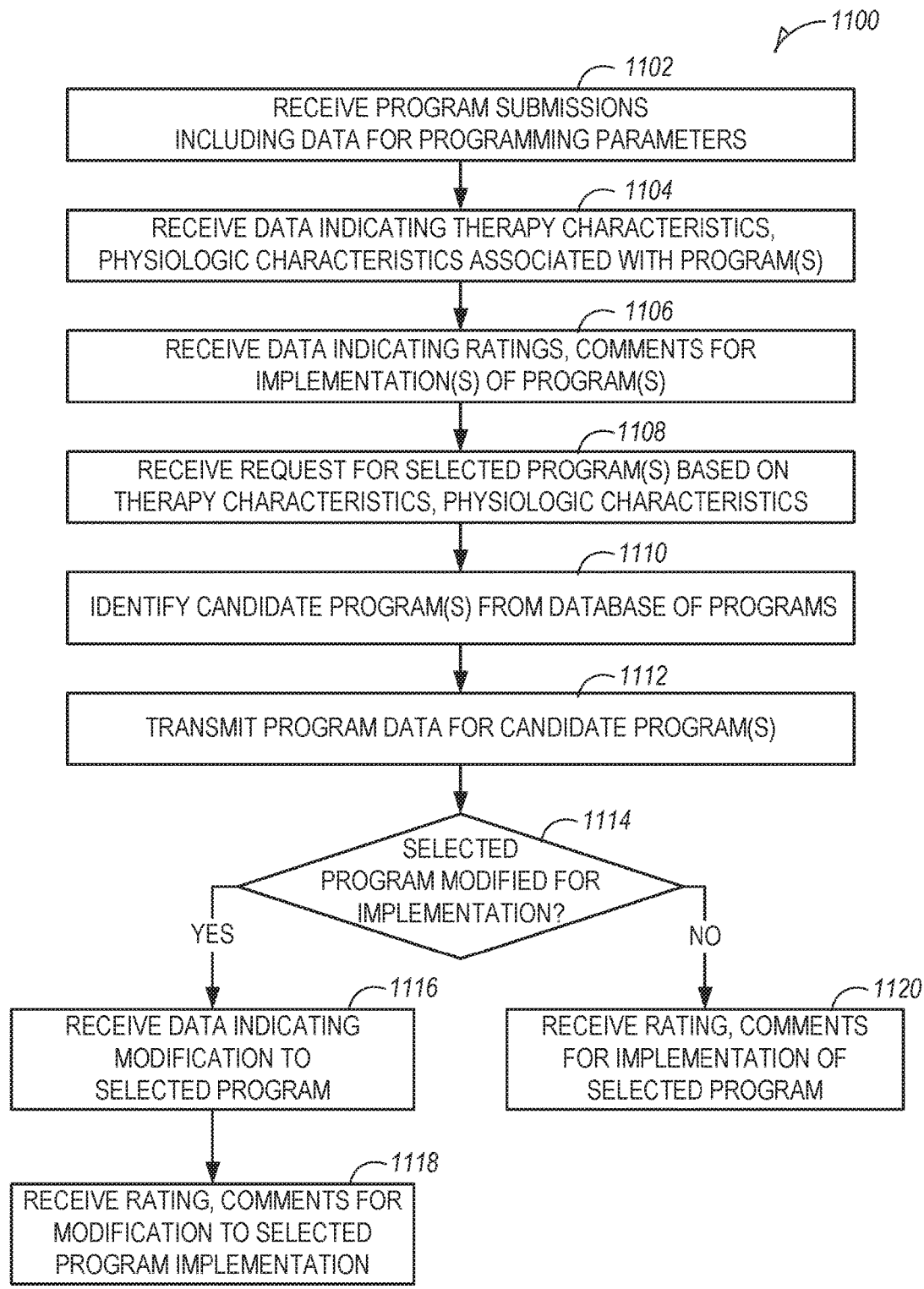
FIG. 11 illustrates, by way of example, an embodiment of a method implemented by a programming guidance information system for maintaining and providing a program of parameters for a neurostimulation device.

FIG. 11 illustrates, by way of example, an embodiment of a method 1100 implemented by a programming guidance information system for maintaining and providing a program of parameters for a neurostimulation device. This method 1100 may be implemented with use of electronic operations within a programming guidance information system, such as with the system 710 and the system interface 906 discussed above.

For example, the programming guidance information system can operate to receive respective program submissions from a plurality of medical facilities and a plurality of medical treatments, including data for programming parameters and programming parameter values (operation 1102). The respective program submissions can be accompanied by data (or data provided at a subsequent time) that indicates therapy characteristics and physiologic characteristics associated with the respective programs (operation 1104), and ratings and comments for respective implementations of the respective programs (operation 1106).

The programming guidance information system can further operate to receive and process a request, originating from a clinical guidance user interface, for a neurostimulation program based on one or both of therapy characteristics and physiologic characteristics (operation 1108). The programming guidance information system operates to identify one or more candidate programs from a database, data source, or data service (operation 1110) using the identification techniques described above. The programming guidance information system then operates to transmit program data for one or more of the candidate programs to the clinical guidance user interface (operation 1112).

The programming guidance information system can further operate to receive modifications and subsequent evaluation of a selected neurostimulation program that is implemented in a neurostimulation device. If a selected program is modified for implementation (evaluation 1114), the programming guidance information system can receive data indicating the modification of the parameter (and the parameter value) in the selected program (operation 1116) and receive a rating or comments related to the modification in the selected program (operation 1118). If the selected program is not is modified for implementation (evaluation 1114), the programming guidance information system can receive data indicating the rating or comments for the selected program (operation 1120), such as at the time of a follow-up evaluation.

Figure 12:
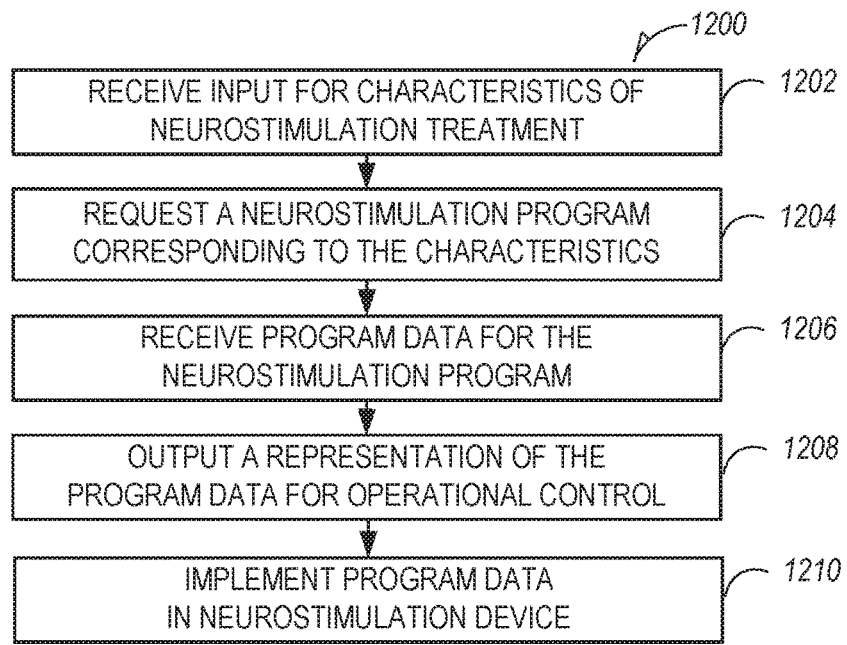
FIG. 12 illustrates, by way of example, an embodiment of a processing method implemented with a clinical guidance software application and electronic system.

FIG. 12 illustrates, by way of example, an embodiment of a processing method 1200 implemented with a clinical guidance software application and electronic system. For example, the processing method 1200 can be embodied by electronic operations performed by one or more computing systems or devices that are specially programmed to implement the clinical guidance user interface described herein.

For example, the method 1200 includes the receipt of input in the clinical guidance user interface, the input including the characteristics of neurostimulation treatment programming (operation 1202) such as physiological information and therapy information. The clinical guidance user interface receives or generates a request for a neurostimulation program, requested from the programming guidance information system, for a program or program settings that corresponds to the characteristics of the neurostimulation treatment (operation 1204).

In response to the request, the programming guidance information system provides data (e.g., program data) for the neurostimulation program that is received and processed by the clinical guidance user interface (operation 1206). A representation of the program data is generated and output (operation 1208), such as may be output by the clinical graphical user interface, provided to an external programming device, or used by other components of a neurostimulation system. Ultimately, the program data is implemented in the neurostimulation device (operation 1210), such as by programming a neurostimulation device using the neuromodulation parameter set of the received program to stimulate a patient.

Figure 13:
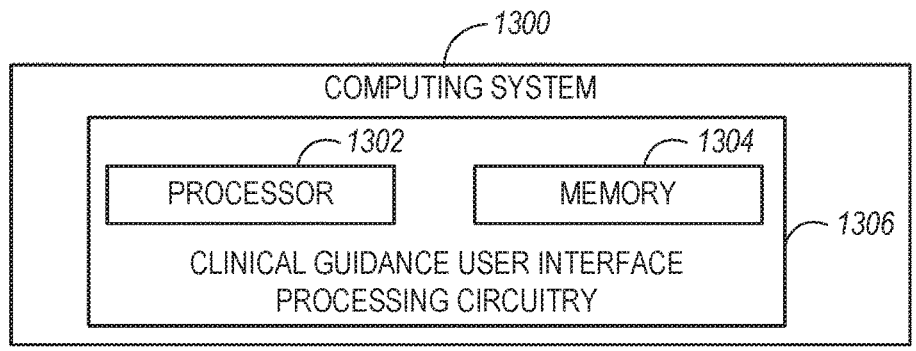
FIG. 13 illustrates, by way of example, a block diagram of an embodiment of a computing system for implementing a clinical guidance user interface.

FIG. 13 illustrates, by way of example, a block diagram of an embodiment of a computing system for implementing a clinical guidance user interface. The system 1300 may be a remote control or other external device used by a clinician, including an unregulated device (e.g., off-the-shelf PC or tablet) used for accessing an internet-connected service hosting a plurality of neurostimulator programs and program information. Alternatively, the system 1300 may be a server or cloud-based device, a network appliance, or other networked device connected via a network (or combination of networks) to a user device. The network may include local, short-range, or long-range networks, such as Bluetooth, cellular. IEEE 802.11 (Wi-Fi), or other wired or wireless networks.

The system 1300 includes a processor 1302 and a memory 1304, which can be optionally included as part of clinical guidance user interface processing circuitry 1306. The processor 1302 may be any single processor or group of processors that act cooperatively. The memory 1304 may be any type of memory, including volatile or non-volatile memory. The memory 1304 may include instructions, which when executed by the processor 1302, cause the processor 1302 to implement the features of the user interface, or to enable other features of the clinical guidance user interface processing circuitry 1306. Thus, electronic operations in the system 1300 may be performed by the processor 1302 or the circuitry 1306.

For example, the processor 1302 or circuitry 1306 may implement any of the features of the method 1200 (including operations 1202, 1204, 1206, 1208, and 1210) to receive clinician input, request a neurostimulation program, receive program data for the neurostimulation program, and output a representation of the neurostimulation program. The processor 1302 or circuitry 1306 may further program a neuromodulator using the optimal neuromodulation parameter set to stimulate a patient. It will be understood that the processor 1302 or circuitry 1306 may also implement features of the method 1000, and other aspects of the clinical guidance user interface described above with reference to FIGS. 6-11.

Figure 14:
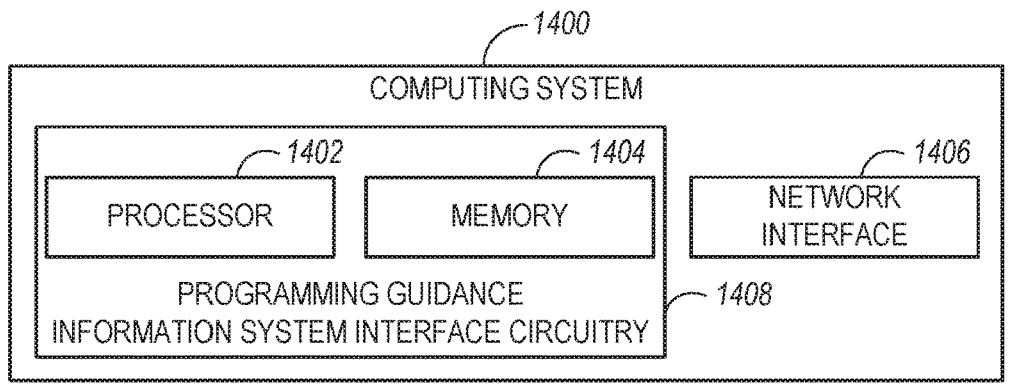
FIG. 14 illustrates, by way of example, a block diagram of an embodiment of a computing system for implementing a programming guidance information system interface.

FIG. 14 illustrates, by way of example, a block diagram of an embodiment of a computing system for implementing a programming guidance information system interface. The system 1400 may be an electronic information service operated by a clinician, a medical facility, a research institution, a medical device manufacturer or distributor, and embodied in a number of different computing platforms. The system 1400 may be a server or cloud-based device, a network appliance, or other networked device connected via a network (or combination of networks) to a user device (e.g., a clinical guidance user interface device). The network may include local, short-range, or long-range networks, such as Bluetooth, cellular, IEEE 802.11 (Wi-Fi), or other wired or wireless networks.

The system 1400 includes a processor 1402 and a memory 1404, which can be optionally included as part of programming guidance information system interface circuitry 1406. The processor 1402 may be any single processor or group of processors that act cooperatively. The memory 1404 may be any type of memory, including volatile or non-volatile memory. The memory 1404 may include instructions, which when executed by the processor 1402, cause the processor 1402 to implement the features of the information system, or to enable other features of the programming guidance information system interface circuitry 1406. Thus, the following references to electronic operations in the system 1400 may be performed by the processor 1402 or the circuitry 1406.

For example, the processor 1402 or circuitry 1406 may implement server-based features corresponding to the method 1200 (including operations 1202, 1204, 1206, 1208, and 1210) to process clinician input, retrieve a neurostimulation program, select program data for the neurostimulation program, and provide data for use in output of a representation of the program. The processor 1402 or circuitry 1406 may further provide data to assist the programming of the neurostimulator using an optimal selected neuromodulation parameter set to stimulate a patient. It will be understood that the processor 1402 or circuitry 1406 may also implement features of the method 1100, and other aspects of the programming guidance information system and system interface described above with reference to FIGS. 7-11.

Figure 15:
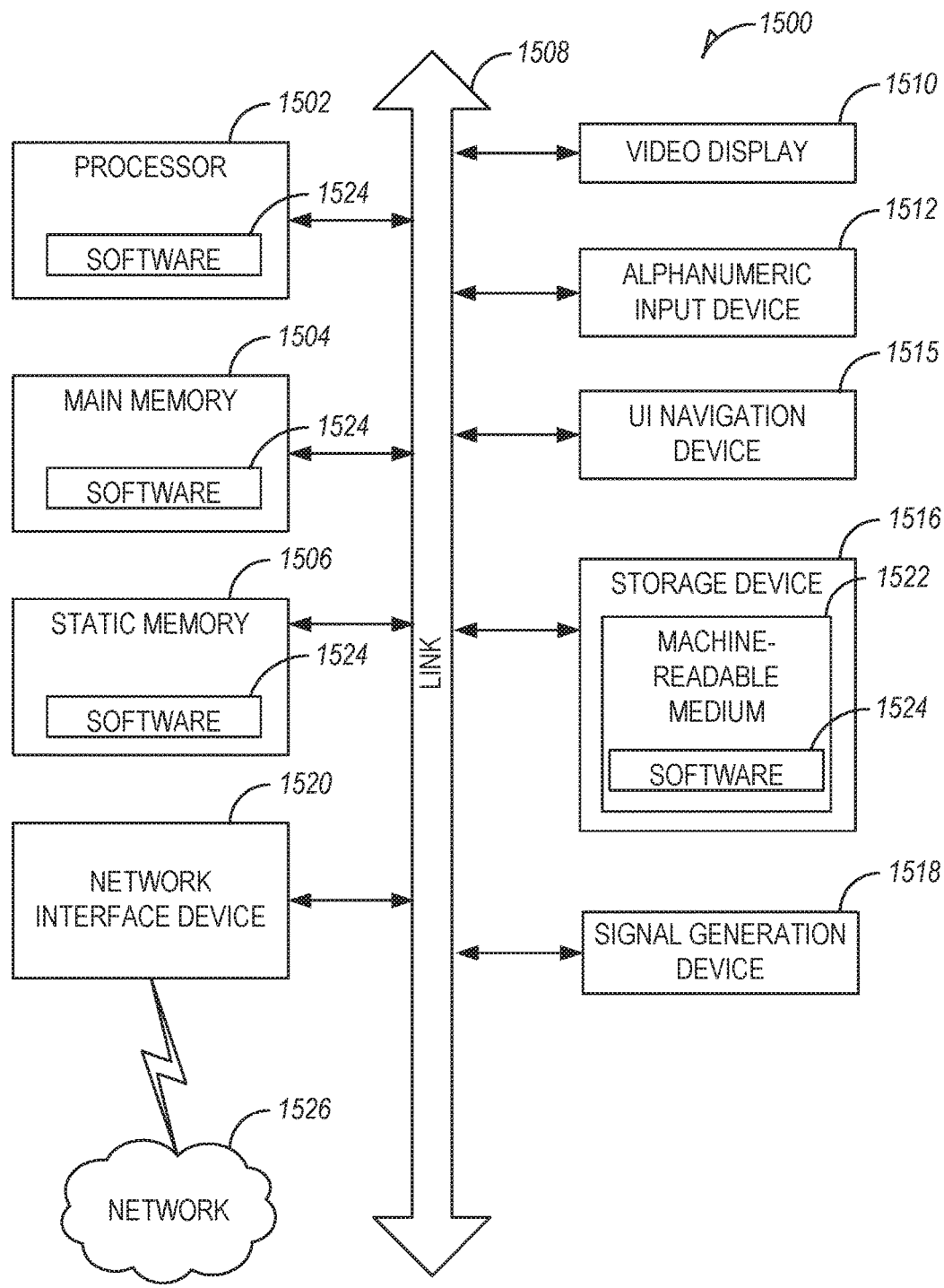
FIG. 15 is a block diagram illustrating a machine in the example form of a computer system, within which a set or sequence of instructions may be executed to cause the machine to perform any one of the methodologies discussed herein, according to an example embodiment.

FIG. 15 is a block diagram illustrating a machine in the example form of a computer system 1500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1500 includes at least one processor 1502 (e.g., a central processing unit (CPU), a graphics processing unit (GPU) or both, processor cores, compute nodes, etc.), a main memory 1504 and a static memory 1506, which communicate with each other via a link 1508 (e.g., bus). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are incorporated into a touch screen display. The computer system 1500 may additionally include a storage device 1516 (e.g., a drive unit), a signal generation device 1518 (e.g., a speaker), a network interface device 1520, and one or more sensors (not shown), such as a global positioning system (GPS) sensor, compass, accelerometer, or other sensor.

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 also constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A device, comprising:
user interface processing circuitry, implemented with a processor and a memory, the user interface processing circuitry to perform electronic operations with the device to:
receive, in a graphical user interface, a clinician input of physiological information and therapy information for neurostimulation treatment of a human subject using a neurostimulation device;
request, from a programming guidance information system, a listing of at least two neurostimulation programs that correspond to the physiological information and the therapy information, wherein the physiological and therapy information indicate characteristics of the neurostimulation treatment attempted with the neurostimulation device for the human subject;
receive, from the programming guidance information system, program data, rating data, and comment data of the at least two neurostimulation programs that are selected by the programming guidance information system as corresponding to the characteristics of the physiological information and the therapy information; and
output, in the graphical user interface, a representation of the program data for each of the at least two received neurostimulation programs;
wherein each respective representation of the program data is accompanied by a representation of the rating data and the comment data in the graphical user interface, wherein the representation of the rating data and the comment data depicts clinician ratings and comments provided from multiple implementations of a corresponding program in other patients;
wherein each of the at least two neurostimulation programs includes a plurality of programmable parameter settings for operational control of the neurostimulation device, and wherein the program data includes respective parameter values established for the plurality of programmable parameter settings; and
wherein the programming guidance information system further selects or ranks the at least two neurostimulation programs on the basis of clinician characteristics for a clinician responsible for the neurostimulation treatment being matched to clinician characteristics for clinicians responsible for neurostimulation treatments of other patients using the respective neurostimulation programs, and wherein the clinician characteristics include at least one of: performance of similar treatments, a common type of medical facility, a common type of medical practice, or social network connections among clinicians or facilities.

2. The device of claim 1,
wherein the request for the neurostimulation programs is communicated to the programming guidance information system, the request including data that represents the physiological information and data that represents the therapy information,
wherein the physiological information indicates one or more of: a medical condition, pain, or medical symptoms of the human subject, and
wherein the therapy information indicates one or more of: a type of the neurostimulation device, a state of the neurostimulation device, respective locations for placements of leads of the neurostimulation device in the human subject, or a type of the leads and a number of the leads of the neurostimulation device in the human subject.

3. The device of claim 1, wherein the plurality of programmable parameter settings include settings for one or more of: pulse patterns, pulse shapes, or a spatial location, of pulses of modulated energy provided with a plurality of leads of the neurostimulation device.

4. The device of claim 1, wherein the plurality of programmable parameter settings include settings for two or more of: a frequency, a pulse width, a number of pulses within a burst or train of pulses, the train-to-train interval, the burst frequency of trains of pulses, a pulse duty cycle, or a burst duty cycle, of the pulses of modulated energy provided with a plurality of leads of the neurostimulation device.

5. The device of claim 1,
wherein the representation of the program data includes a listing of the neurostimulation programs, and
wherein the listing is ordered based on the respective clinician ratings and comments for the respective neurostimulation programs.

6. The device of claim 1,
wherein the programming guidance information system is accessible via a network connection, and wherein the programming guidance information system includes a data interface accessible via the network connection to receive the request for the neurostimulation programs and transmit the program data of the neurostimulation programs in response to the request, and
wherein the programming guidance information system is operable to select one of the neurostimulation programs from among a plurality of candidate neurostimulation programs represented in remote data storage accessible to the programming guidance information system.

7. The device of claim 6,
wherein the neurostimulation programs are selected by the programming guidance information system based on a number of matches to stored characteristics of the neurostimulation programs.

8. The device of claim 1, the user interface processing circuitry to further perform electronic operations with the device to:
receive, in the graphical user interface, a clinician input of a rating and a comment for an update to a particular one of the neurostimulation programs;
transmit, to the programming guidance information system, updated program data for the update to the particular one of the neurostimulation programs; and
transmit, to the programming guidance information system, data representing the rating and the comment for the update to the particular one of the neurostimulation programs;
wherein the program data is used in an initial programming of the neurostimulation device, and wherein the update to the particular one of the neurostimulation programs is provided from clinician modification of one or more of the plurality of programmable parameter settings of the particular one of the neurostimulation programs.

9. The device of claim 1, wherein the graphical user interface provides an input screen to receive the clinician input of the physiological information and the therapy information and an output screen to output the representation of the program data of the neurostimulation programs.

10. The device of claim 1, the user interface processing circuitry to further perform electronic operations with the device to:
transmit a selected set of the plurality of programmable parameter settings to a programming device, the programming device to program the neurostimulator device using the selected set of the plurality of programmable parameter settings.

11. A method, comprising a plurality of electronic operations executed with a processor and memory of a computer system, the plurality of electronic operations including:
receiving, in a graphical user interface, a clinician input of physiological information and therapy information for neurostimulation treatment of a human subject using a neurostimulation device;
requesting, from a programming guidance information system, a listing of at least two neurostimulation programs that correspond to the physiological information and the therapy information, wherein the physiological and therapy information indicate characteristics of the neurostimulation treatment attempted with the neurostimulation device for the human subject;
receiving, from the programming guidance information system, program data, rating data, and comment data of the at least two neurostimulation programs that are selected by the programming guidance information system as corresponding to the characteristics of the physiological information and the therapy information; and
outputting, in the graphical user interface, a representation of the program data for each of the neurostimulation program;
wherein each respective representation of the program data is accompanied by a representation of the rating data and the comment data in the graphical user interface, wherein the representation of the rating data and the comment data depicts clinician ratings and comments provided from multiple implementations of a corresponding program in other patients;
wherein each of the at least two neurostimulation programs includes a plurality of programmable parameter settings for operational control of the neurostimulation device; and
wherein the programming guidance information system further selects or ranks the at least two neurostimulation programs on the basis of clinician characteristics for a clinician responsible for the neurostimulation treatment being matched to clinician characteristics for clinicians responsible for neurostimulation treatments of other patients using the respective neurostimulation programs, and wherein the clinician characteristics include at least one of: performance of similar treatments, a common type of medical facility, a common type of medical practice, or social network connections among clinicians or facilities.

12. The method of claim 11,
wherein the request for the neurostimulation programs is communicated to the programming guidance information system, the request including data that represents the physiological information and data that represents the therapy information,
wherein the physiological information indicates one or more of: a medical condition, pain, or medical symptoms of the human subject, and
wherein the therapy information indicates one or more of: a type of the neurostimulation device, a state of the neurostimulation device, respective locations for placements of leads of the neurostimulation device in the human subject, or a type of the leads and a number of the leads of the neurostimulation device in the human subject.

13. The method of claim 11, wherein the plurality of programmable parameter settings include settings for one or more of: pulse patterns, pulse shapes, or a spatial location, of pulses of modulated energy provided with a plurality of leads of the neurostimulation device.

14. The method of claim 11,
wherein the representation of the program data includes a listing of the neurostimulation programs, and
wherein the listing is ordered based on the respective clinician ratings and comments for the respective neurostimulation programs.

15. The method of claim 11,
wherein the programming guidance information system is accessible to the computer system via a network connection, and wherein the programming guidance information system includes a data interface accessible via the network connection to receive the request for the neurostimulation programs and transmit the program data of the neurostimulation programs to the computer system in response to the request, and
wherein the neurostimulation programs are selected by the programming guidance information system based on matching a plurality of characteristics of the physiological information and the therapy information to characteristics of the neurostimulation programs.

16. The method of claim 11, the electronic operations further including:
receiving, in the graphical user interface, a clinician input of a rating and a comment for an update to a particular one of the neurostimulation programs;
transmitting, to the programming guidance information system, updated program data for the update to the particular one of the neurostimulation programs; and
transmitting, to the programming guidance information system, data representing the rating and the comment for the update to the particular one of the neurostimulation programs;
wherein the program data is used in an initial programming of the neurostimulation device, and wherein the update to the particular one of the neurostimulation programs is provided from clinician modification of one or more of the plurality of programmable parameter settings of the particular one of the neurostimulation programs.

17. The method of claim 11, the electronic operations further including:
transmitting a selected set of the plurality of programmable parameter settings to a programming device, the programming device to program the neurostimulator device using the selected set of the plurality of programmable parameter settings.

18. A non-transitory machine-readable medium including instructions, which when executed by a machine, cause the machine to:
receive, in a graphical user interface, a clinician input of physiological information and therapy information for neurostimulation treatment of a human subject using a neurostimulation device;
request, from a programming guidance information system, a listing of at least two neurostimulation programs that correspond to the physiological information and the therapy information, wherein the physiological and therapy information indicate characteristics of the neurostimulation treatment attempted with the neurostimulation device for the human subject;

receive, from the programming guidance information system, program data, rating data, and comment data of the at least two neurostimulation programs that are selected by the programming guidance information system as corresponding to the characteristics of the physiological information and the therapy information; and output, in the graphical user interface, a representation of the program data of the neurostimulation program;

wherein each respective representation of the program data is accompanied by a representation of the rating data and the comment data in the graphical user interface, wherein the representation of the rating data and the comment data depicts clinician ratings and comments provided from multiple implementations of a corresponding program in other patients;

wherein each of the at least two neurostimulation programs includes a plurality of programmable parameter settings for operational control of the neurostimulation device; and wherein the programming guidance information system further selects or ranks the at least two neurostimulation programs on the basis of clinician characteristics for a clinician responsible for the neurostimulation treatment being matched to clinician characteristics for clinicians responsible for neurostimulation treatments of other patients using the respective neurostimulation programs, and wherein the clinician characteristics include at least one of: performance of similar treatments, a common type of medical facility, a common type of medical practice, or social network connections among clinicians or facilities.

19. The machine-readable medium of claim 18, wherein the representation of the program data includes a listing of the neurostimulation programs and a plurality of additional neurostimulation programs, the additional neurostimulation programs corresponding to the physiological information and the therapy information, and wherein the listing is ordered based on the respective clinician ratings and comments for the respective neurostimulation programs.

* * * * *